United States Patent
Lin et al.

(10) Patent No.: US 8,366,704 B2
(45) Date of Patent: Feb. 5, 2013

(54) OPTICAL DEVICES AND METHODS FOR SELECTIVE AND CONVENTIONAL PHOTOCOAGULATION OF THE RETINAL PIGMENT EPITHELIUM

(75) Inventors: Charles P. Lin, Arlington, MA (US); Clemens Alt, Watertown, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 13/480,955

(22) Filed: May 25, 2012

(65) Prior Publication Data

US 2012/0296320 A1     Nov. 22, 2012

Related U.S. Application Data

(63) Continuation of application No. 11/263,677, filed on Oct. 31, 2005, now Pat. No. 8,187,257, which is a continuation-in-part of application No. 10/296,417, filed as application No. PCT/US01/17818 on Jun. 1, 2001, now Pat. No. 7,115,120.

(60) Provisional application No. 60/209,010, filed on Jun. 1, 2000.

(51) Int. Cl.
    *A61B 18/18*     (2006.01)
(52) U.S. Cl. .................. 606/10; 606/4; 606/17; 607/88
(58) Field of Classification Search .................. 606/3–6, 606/10–13, 16–19; 607/88, 89; 351/205–212
    See application file for complete search history.

(56) References Cited

U.S. PATENT DOCUMENTS

| | | |
|---|---|---|
| 4,644,948 A | 2/1987 | Lang et al. |
| 4,758,081 A | 7/1988 | Barnes |
| 5,029,220 A | 7/1991 | Juday |
| 5,254,112 A | 10/1993 | Sinofsky et al. |
| 5,302,259 A | 4/1994 | Birngruber |
| 5,430,509 A | 7/1995 | Kobayashi |
| 5,459,570 A | 10/1995 | Swanson et al. |
| 5,549,596 A | 8/1996 | Latina |
| 5,549,599 A | 8/1996 | Sumiya |
| 5,620,437 A | 4/1997 | Sumiya |
| 5,778,133 A | 7/1998 | Plesko |
| 5,782,822 A | 7/1998 | Telfair et al. |
| 5,997,141 A | 12/1999 | Heacock |
| 6,110,165 A * | 8/2000 | Ota ................................ 606/4 |

(Continued)

FOREIGN PATENT DOCUMENTS

| | | |
|---|---|---|
| JP | 2001149403 | 6/2001 |
| WO | WO 99/65431 | 12/1999 |
| WO | WO01/91661 | 12/2001 |
| WO | WO2004/043234 | 5/2004 |
| WO | WO2005/065116 | 7/2005 |

OTHER PUBLICATIONS

Search Report in European Patent Application No. 06827308.5, dated May 21, 2012.

(Continued)

*Primary Examiner* — Ahmed Farah
(74) *Attorney, Agent, or Firm* — Fish & Richardson P.C.

(57) ABSTRACT

The present invention provides devices and methods for applying radiation to the retina of a patient. In one embodiment, an apparatus includes a radiation source for generating a radiation beam suitable for absorption by retinal pigment epithelial cells. One or more optical components are included to direct the beam onto the retina. A scanner is optically coupled to the radiation source to control movement of the beam in two dimensions to allow a scan over the retina. A controller applies control signals to the scanner to adjust beam movement to illuminate a plurality of retinal locations in a temporal sequence according to a predefined pattern. The device can be operated in one mode to effect selective targeting of retinal pigment epithelial cells, or in another mode to effect thermal photocoagulation of the retina.

10 Claims, 12 Drawing Sheets

U.S. PATENT DOCUMENTS

| | | | |
|---|---|---|---|
| 6,186,628 B1 * | 2/2001 | Van de Velde | 351/205 |
| 6,325,792 B1 | 12/2001 | Swinger et al. | |
| 6,428,532 B1 | 8/2002 | Doukas et al. | |
| 6,610,051 B2 | 8/2003 | Bille | |
| 6,671,043 B1 | 12/2003 | Huettman | |
| 6,706,036 B2 | 3/2004 | Lai | |
| 6,743,221 B1 | 6/2004 | Hobart et al. | |
| 6,887,232 B2 | 5/2005 | Bille | |
| 7,115,120 B2 | 10/2006 | Lin | |
| 7,354,432 B2 * | 4/2008 | Eells et al. | 606/4 |
| 7,763,017 B2 | 7/2010 | Lin | |
| 7,766,903 B2 * | 8/2010 | Blumenkranz et al. | 606/4 |
| 8,187,257 B2 * | 5/2012 | Lin et al. | 606/10 |
| 2004/0102765 A1 | 5/2004 | Koenig | |
| 2004/0176752 A1 | 9/2004 | Alfano et al. | |
| 2005/0021013 A1 | 1/2005 | Visuri et al. | |
| 2005/0197655 A1 | 9/2005 | Telfair et al. | |

OTHER PUBLICATIONS

English translation of the Japanese Office Action dated Sep. 20, 2011, in Japanese application No. 2008-538118.

Kelly et al., "Microcavitation and Cell Injury in RPE Cells Following Short-Pulsed Laser Irradiation", *SPIE* 2975:174-179 (1997).

Lin et al., "Selective Cell Killing by Microparticle Absorption of Pulsed Laser Radiation", *IEEE J. Sel. Topics Quantum Elect.* 5(4):963-968 (1999).

Vogel et at., Ophthalmology; vol. 93, No. 10, pp. 1259-1269, Oct. 1986.

Juhasz et al., Lasers in Surgery and Medicine; vol. 19, No. 1, pp. 23-31, Jan. 1996.

International Search Report and Written Opinion dated Sep. 17, 2007, for corresponding application No. PCT/US06/42696.

Office Action issued in corresponding Australian application No. 2006308721, filed on Oct. 31, 2006.

\* cited by examiner

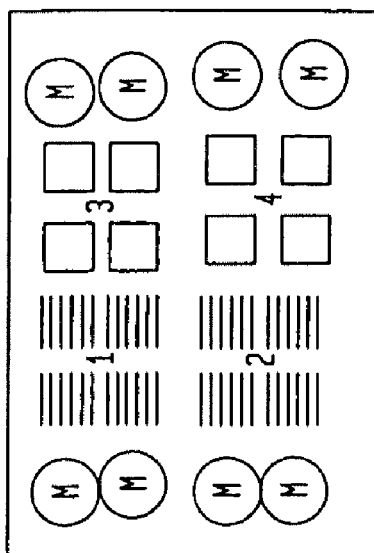
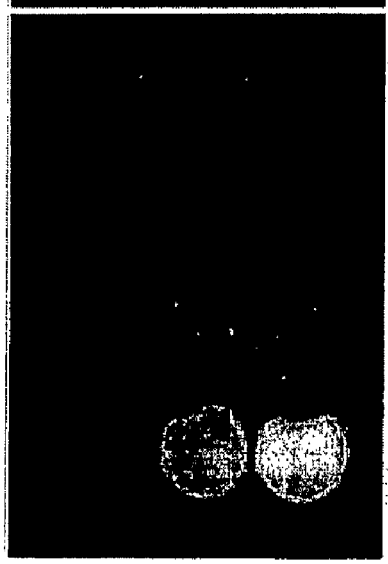
FIG. 8C
FIG. 8B
FIG. 8A

OPTICAL DEVICES AND METHODS FOR SELECTIVE AND CONVENTIONAL PHOTOCOAGULATION OF THE RETINAL PIGMENT EPITHELIUM

CROSS-REFERENCE TO RELATED APPLICATIONS

This application is a continuation of, and claims priority to, U.S. patent application Ser. No. 11/263,677, filed on Oct. 31, 2005, now U.S. Pat. No. 8,187,257, which is a continuation-in-part of U.S. patent application Ser. No. 10/296,417, filed on Jul. 9, 2003 and issued as U.S. Pat. No. 7,115,120, which in turn is a U.S. national stage application of PCT Patent Application No. PCT/US01/17818, filed on Jun. 1, 2001, which in turn claims priority to U.S. Provisional Patent Application No. 60/209,010, filed on Jun. 1, 2000. The entire contents of each of the foregoing applications are incorporated herein by reference.

STATEMENT AS TO FEDERALLY SPONSORED RESEARCH

This invention was made with Government support under Contract No. F49620-00-1-0179 awarded by AFOSR and Contract No. EY12970-03 awarded by NIH. The Government has certain rights in the invention.

BACKGROUND OF THE INVENTION

The present invention relates generally to optical devices as well as methods for applying treatment radiation to the eye, and more particularly, to such devices and methods for applying treatment radiation to the retina.

Retinal laser photocoagulation is one of the most commonly applied treatment modalities. To achieve photocoagulation, a single laser pulse of green wavelength (typically at a wavelength of 514 nm or 532 nm) can be applied to the retina such that the light is absorbed and converted to heat by compact granules of melanin (melanosomes) that are located in retinal pigment epithelial (RPE) cells. As the duration of the laser pulse is typically in a range of 50 ms to 200 ms, the generated heat diffuses from those absorbers to other structures, leading to thermal coagulation of the retina. The retinal photocoagulation can be utilized in treatment of retinal diseases where scar formation and/or high radiant exposure are required (e.g., retinal detachment, diabetic retinopathy).

The retinal photocoagulation, however, can cause coagulation of photoreceptors, thus leading to blind spots and loss of visual sense. As such, this treatment modality is not suitable for application to the macula, especially the fovea. To remedy this shortcoming, selective photocoagulation of RPE cells by employing short laser pulses was developed as a therapeutic modality for those retinal diseases that are believed to be mainly caused by a dysfunction of the RPE. This treatment modality, commonly known as selective retinal therapy (SRT), uses short laser pulses to target RPE cells while preserving the adjacent photoreceptors in the neurosensory retina.

Although considerable progress has been made in the above techniques and in the design of optical devices for performing them, a need still exists for enhanced optical devices and methods for performing photocoagulation as well as selective targeting of RPE cells.

There is also a need for such optical devices and methods that provide more efficient ways of applying those treatment modalities. Further, there is need for such devices that can be readily configured for application of one treatment modality or the other.

SUMMARY OF THE INVENTION

One aspect of the present invention provides an apparatus for applying radiation to a subject's (e.g., a patient's) retina. The apparatus includes a radiation source for generating a beam of radiation having one or more wavelengths that are suitable for absorption by retinal pigment epithelial (RPE) cells, and at least one optical component for directing the beam onto the patient's retina. The apparatus also includes a scanner that is coupled to the source for controllably moving the beam in two dimensions so as to allow the beam to scan the retina. A controller applies control signals to the scanner so as to adjust the movement of the beam so that it can illuminate one or more retinal locations in a temporal sequence according to a predefined pattern. The predefined pattern can include at least the following two patterns: one characterized by a separated line pattern, and another characterized by an interlaced line pattern.

In a related aspect, the controller is capable of operating the scanner in at least two scan modes, one of which is suitable for selective targeting of RPE cells and the other is suitable for causing retinal thermal photocoagulation. A user interface can also be included that allows a user to communicate with the controller for selecting one, or the other, of the scan modes.

In general, in many embodiments of the invention, selective targeting of the RPE cells can be achieved by adjusting one or more parameters associated with radiation illuminating the retina so as to minimize the diffusion of heat deposited in the illuminated RPE cells away from those cells, e.g., to the adjacent photoreceptors. Those parameters can include, e.g., the fluence of the radiation deposited on the retina (which, in turn, can depend on the power of the radiation beam, its cross-sectional size at the retina, and the dwell time of the beam as it is scanned over the retina), a utilized scan pattern, and the number of repetitions of the scan pattern. In many embodiments of the optical devices of the invention, one or more of those parameters can be controlled so as to achieve selective targeting the RPE cells, as discussed in more detail below. For example, heat diffusion from the RPE cells to adjacent structures (e.g., photoreceptors) can be minimized by employing short dwell times and/or a scan pattern characterized by illuminated locations being separated by non-illuminated locations within a retinal target area (e.g., a separated line pattern), and/or a low number of repetitions of a scan pattern. By way of example, in some embodiments of the invention, selective targeting of the RPE cells can be achieved by employing a separated line pattern (SEP) with a beam dwell time in a range of about 1 nanosecond to about 50 microseconds (µs) at an incident fluence less than about 10,000 mJ/cm² (e.g., in a range of about 50 mJ/cm² to about 10,000 mJ/cm²) with about, e.g., 10 repetitions of the scan pattern. Alternatively, selective targeting of the RPE cells can be achieved by employing an interlaced line pattern (INT) with a beam dwell time in a range of about 1 ns to about 15 µs at an incident fluence of less than about 2000 mJ/cm² (e.g., in a range of about 50 mJ/cm² to about 2000 mJ/cm²). In contrast to selective targeting of the RPE cells, retinal thermal photocoagulation can be achieved by adjusting the above parameters to facilitate heat diffusion away from the illuminated RPE cells to adjacent structures. For example, photocoagulation can be achieved by utilizing a low beam scan velocity and/or a scan pattern characterized by illumination of an entire (or substantially an entire) retinal target area (e.g., an interlaced line pattern) so that heat deposited in an RPE layer diffuses more readily to adjacent structures rather than within the layer itself, and/or employing a high repetition rate. By way of example, in some embodiments, retinal photocoagulation can be achieved by employing a separated line pattern with a beam dwell time equal to or longer than about 50 µs at an incident fluence equal to or greater than about 10,000 mJ/cm$^2$ with, e.g., about 10 repetitions of the scan pattern. Alternatively, retinal photocoagulation can be achieved by employing an interlaced line pattern (INT) with a beam dwell time equal to or longer than about 15 µs at an incident fluence equal to or greater than about 2000 mJ/cm$^2$. Further, in many embodiments, in both selective targeting mode and the photocoagulation mode, an incident fluence that is equal to or greater than about 50 mJ/cm$^2$ is preferably employed.

In a related aspect of the invention, the controller provides control signals to the radiation source, and/or optical elements coupled to that source, to adjust the beam's fluence (e.g., through adjusting the beam power and/or dimension). These control signals can be utilized, e.g., in combination with control signals applied to the scanner, to provide selective targeting of the RPE cells or conventional photocoagulation. Further, the controller can apply trigger signals to the scanner and/or the source to initiate, or repeat, a retinal scan.

In a related aspect, the beam can have a cross-sectional dimension (e.g., a diameter) in a range of about 5 microns to about 50 microns, or in a range of about 5 microns to about 30 microns. In some cases, e.g., in the selective targeting mode, the beam's cross sectional dimension is about the size of an RPE cell.

The radiation source can be, e.g., a laser generating continuous-wave radiation. In some embodiments, the radiation source can emit continuous-wave radiation that includes wavelengths in a range of about 400 nanometers to about 700 nanometers, or in a range of about 500 nm to about 600 nm.

In related aspects of the invention, some optical components of the apparatus include one or more focusing optical elements that are optically coupled to the scanner for focusing a radiation beam onto a patient's retina, e.g., after the beam's passage through the scanner. In some cases, the optical components can include one or more optical reflective elements that direct that beam onto the patient's retina.

In another aspect of the invention, the scanner can include one or more beam deflecting devices. In many embodiments, each beam deflecting device can be configured to scan the radiation beam in one of the scanning dimensions. Possible beam deflecting devices suitable for use in the practice of the invention include, without limitation, acousto-optic deflectors (AODs), galvanometer scanners, rotating polygons, and resonance scanners. The controller can apply predefined control signals to the beam deflecting device so as to cause beam movement along one scanning dimension. In such an instance, the controller can also include a memory module for storing one or more predefined control waveforms for application to the AOD, or other suitable beam deflecting devices. For example, a predefined control waveform can cause the beam to move in accordance with a predefined speed. In some embodiments, the scanner includes two AODs that are mounted orthogonal to one another, and operate under the control of the controller, to provide a two-dimensional scan of the beam.

The scanner can also include an intensity switch, which can be operated under the control of the controller, for selectively switching on and off the intensity of the radiation beam propagated through it. In such an instance, the controller can include a beam activation signal generator for sending a switching signal to the intensity switch. The activation signal generator can provide signals to the intensity switch for selectively switching the intensity of the propagated beam on and off based, e.g., on control signals applied to the scanner. In some embodiments, the activation signal generator is implemented as a window comparator.

A targeting device can also be included for viewing the retina (e.g., before, during, or after one or more scans) and/or directing the beam onto the retina. Potential targeting devices include, without limitation, a microscope, a slit lamp, and a laser scanning ophthalmoscope.

Another aspect of the present invention provides an optical system for applying radiation to the eye of a subject (e.g., a patient). The system includes a source for generating a radiation beam suitable for absorption by RPE cells of the eye. One or more optical components are included in the system for directing the beam onto the eye. The system also includes a scanner optically coupled to the source for moving the beam. The scanner can move the beam along two mutually orthogonal dimensions, each dimension being orthogonal to a propagation axis of the beam. In addition, the system includes a controller for applying control signals to the scanner for adjusting the beam movement. The beam can be moved (scanned) over the retina so as to illuminate one or more retinal locations in a temporal sequence in accordance with one of at least two scan modes.

In a related aspect of the invention, the controller in the above optical system can apply control signals to the scanner to cause beam movement in accordance with a selected pattern over a selected target area of the retina. The pattern can correspond to illuminating substantially an entire retinal target area requiring treatment, or can correspond to illuminating portions of that target area such that the illuminated portions are separated from one another by non-illuminated portions of the target area.

In a related aspect of the invention, the scanner in the above optical system can include two beam deflecting devices, one of which is capable of scanning the beam along one dimension and the other is capable of scanning the beam along another dimension (e.g., an orthogonal dimension). Further, the controller can include at least two signal channels, one of which can apply control signals to one of those beam deflecting devices, and another channel can apply control signals to the other. The controller can also include at least two memory modules: one for storing control signals associated with one of those signal channels and the other for storing control signals associated with the other signal channel.

In another aspect of the present invention, an apparatus is disclosed for applying radiation to the retina, which includes means for generating a radiation beam having one or more wavelengths suitable for absorption by RPE cells, and an optical means for directing the beam to the retina. The apparatus also includes a scanning means, optically connected to the means for generating the radiation beam, for moving the beam on the retina in two dimensions. The apparatus further includes a controlling means that applies control signals to the scanning means for illuminating a plurality of retinal locations in a temporal sequence according to a scan mode. The controlling means can illuminate the retinal locations in at least two scan modes. One of the scan modes can be suitable for selective targeting of the RPE cells, while another scan mode can be suitable for causing thermal coagulation in the retina.

Another aspect of the present invention is directed to a method for performing photocoagulation. The method includes the step of scanning a continuous wave radiation beam to illuminate one or more retinal locations. The illumination is in a temporal sequence according to a predefined pattern to cause thermal photocoagulation in at least a portion of the retina. The predefined pattern (e.g., an interlaced line pattern) can illuminate substantially all of the retinal target region undergoing photocoagulation. Alternatively, the illuminated location(s) can only be a fraction of the total target region. In the latter instance, the predefined pattern can be, e.g., a separated line pattern.

A further aspect of the present invention provides a method for performing selective targeting of RPE cells. The method includes the step of scanning a continuous wave radiation beam over the retina so as to illuminate one or more retinal locations in a temporal sequence according to a predefined pattern. The beams' fluence and its dwell time at the illuminated locations are selected so as to cause selective targeting of RPE cells at those locations. The predefined pattern (e.g., a separated line pattern) can mix illuminated areas of RPE cells with nonilluminated areas in a target portion of the retina requiring treatment such that the non-illuminated RPE cells remain undamaged (or at least substantially undamaged) by the illumination process, e.g., by heat deposited in the retina by radiation. Further understanding of the invention can be obtained by reference to the following detailed description in conjunction with associated drawings, which are briefly described below:

BRIEF DESCRIPTION OF THE DRAWINGS

FIG. 8A is an image (fundus photograph) of an in vivo scanned area of a rabbit retina minutes after that area is illuminated by a radiation beam using the system of FIG. 7, FIG. 8B is an image (fluorescence angiograph) of an in vivo scanned area of a rabbit retina about one hour after that area is illuminated by a radiation beam using the system of FIG. 7, FIG. 8C depicts a schematic diagram of the types of beam scanning performed on a rabbit retina as photographed in FIGS. 8A and 8B.

DETAILED DESCRIPTION

The present invention provides optical devices and methods for applying treatment radiation to the retina. In one aspect, the invention incorporates within a single optical device the capability of performing selective targeting of retinal pigmented epithelial cells as well as retinal photocoagulation. For example, the optical device can include a controller that can adjust the operating parameters of a beam illuminating the retina (e.g., dwell time and/or power and/or scan pattern and/or number of repetitions of a scan pattern) so as to provide selective targeting of the RPE cells or photocoagulation. Selective targeting of RPE cells refers to utilizing radiation to illuminate one or more RPE cells in a locality to selectively damage the illuminated cells without causing substantial damage to adjacent RPE cells and/or the overlying photoreceptors by confining (spatially and/or temporally) the diffusion of heat generated by the incident radiation. When using a moving radiation beam with a particular dwell time, selective targeting of RPE cells can be achieved when the dwell time is shorter than, or of the order of, the thermal relaxation time of the RPE cells (which is about 5 μs).

The term "dwell time" as applied to a scanning radiation beam is known to those having ordinary skill in the art. To the extent that any further explanation may be needed, the term "dwell time," as used herein, refers to the amount of time a particular location is exposed to a radiation beam during the scan of a beam. For example, if a beam travels with constant velocity $v_0$ and has a circular cross section with a diameter $d_0$, then the dwell time $\tau$ at the center of a scan line is given by:

$$\tau = \frac{d_0}{v_0}$$

As used herein, the term "fluence" refers to the amount of energy per unit area imparted to a target illuminated by a radiation beam during a single radiation exposure.

Figure 1A:
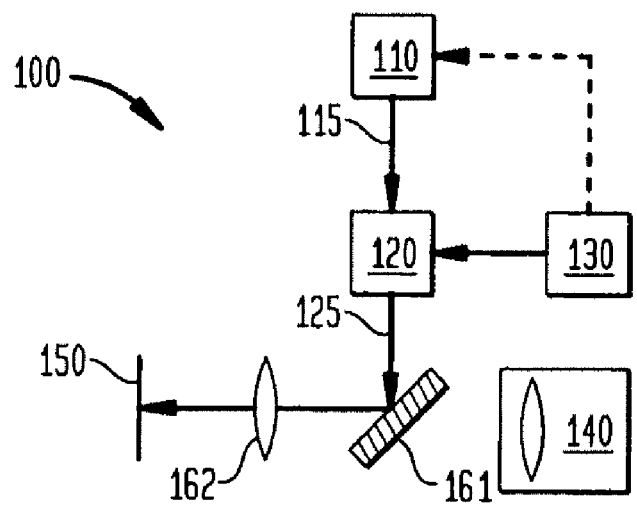
FIG. 1A depicts a schematic diagram of an optical system according to one embodiment of the invention for applying radiation to a retina.

Turning to an illustrated embodiment, FIG. 1A schematically depicts an exemplary optical device 100 in accordance with an exemplary embodiment of the invention that is suitable for applying treatment radiation to a subject's retina. As discussed in more detail below, the optical device 100 can control a radiation beam in a particular manner (e.g., move the beam according to a particular temporal sequence and/or spatial pattern) to treat a subject's eye. More specifically, the optical device can operate in one of at least two treatment modes. For example, one treatment mode selectively targets retinal pigment epithelial (RPE) cells while the other mode achieves retinal thermal photocoagulation.

The selective targeting of the RPE cells is typically characterized by a minimal diffusion of heat deposited in the RPE cells into the adjacent photoreceptors so as to preserve the functioning of the adjacent photoreceptors. When using a moving radiation beam with a particular dwell time, selective targeting of RPE cells can be achieved by selecting the dwell time to be shorter than, or of the order of, the thermal relaxation time (TRT) of the RPE cells (about 5 μs) such that heat diffusion away from the absorbing RPE cells is decreased, and preferably minimized. In contrast, significant heat diffusion from illuminated areas to adjacent areas, resulting from e.g. long exposure times, can facilitate thermal coagulation. Thermal photocoagulation in the retina is characterized by thermal destruction of RPE cells, followed by irreversible coagulation of neural retina tissue. Particular diseases, such as retinal detachment and diabetic retinopathy, can be successfully treated by thermal coagulation. Using a moving beam of radiation, thermal photocoagulation in a retina can be achieved by selecting the beam dwell time to be much longer than the TRT of the RPE cells (e.g., the dwell time can be longer than from about 3 times (using, e.g., INT pattern) to about 10 times (using, e.g., SEP pattern) the TRT of RPE cells.

Turning again to the exemplary device 100, it includes a radiation source 110 that generates a beam of treatment radiation 115 for application to the retina. Possible radiation sources include those capable of producing radiation that is mainly absorbed by melanosomes in the retinal pigment epithelium. More particularly, the radiation generated by the source 110 can include one or more wavelengths suitable for absorption by retinal pigment epithelial cells. In many embodiments, the source 110 is a laser that generates continuous-wave radiation having wavelengths in the visible range (about 400 nm to about 700 nm), and preferably in a range of about 480 nm to about 550 nm. Some examples of such lasers include, without limitation, argon-ion, copper, krypton, Helium-Neon, Nd:YVO$_4$, Nd:YLF and Nd:YAG lasers, in short, any laser that can provide suitable power in the green wavelength range. (e.g., 488 nm, 511 nm, 514 nm, 527 nm and 532 nm, 543 nm, or similar), or any other suitable wavelength range.

With continued reference to FIG. 1A, a scanner 120, which operates under the control of a controller 130, can receive the radiation beam 115 and can cause beam movement in two dimensions. In particular, the scanner can scan the beam in two dimensions that are orthogonal to the beam's propagation direction. The beam 125 after passage through the scanner 120 is directed onto a target location (e.g., a subject's retina) via one or more optical elements. For example, in this illustrative embodiment, the scanner 120 directs the radiation beam onto a mirror 161 that reflects the beam onto a convergent lens 162 that, in turn, focuses the radiation beam onto a specified location 150 (e.g., a portion of a subject's retina). Non-limiting examples of optical devices suitable for directing the beam onto the retina include lenses, gradient index lenses, reflecting devices, beam splitters, attenuators, and collimators or combinations thereof. Optical devices can also be used elsewhere in the optical system to direct a beam as desired (e.g., directing a beam from a radiation source to the scanner using optical elements such as lenses and/or reflective elements or optical light guides, such as optical fibers or combinations thereof).

The exemplary device further includes a targeting device 140, such as a biomicroscope, for aiming the treatment beam onto a target portion of the retina and/or for viewing the target vicinity scanned by the device 100. A medical professional can employ the device 140 to view the area of a patient's retina that is scanned by the device 100 to assess the treatment performed. Other non-limiting examples of targeting devices include slit lamps, laser scanning ophthalmoscopes or any device that can allow visualizing the fundus of the eye. In some embodiments, the treatment device and the targeting device 140 share one or more optical components (e.g., a convergent lens 162). For example, a lens and/or a reflective element can act both as a portion of the targeting device (e.g., a slit lamp) and as an optical component for directing the radiation beam onto a target. In any case, the lens and/or the reflective element can be adjusted such that when the targeting device is focused on a portion of the retina to provide a clear image thereof, the treatment beam is also focused on that retinal portion. In other words, the treatment device and the targeting device can share a plane of focus. In this exemplary embodiment, the mirror 161 is oriented to deflect the beam 125 along the optical axis of the targeting device 140. Further, in some embodiments, the treatment device can be partially or totally integrated within the targeting device 140.

With continued reference to FIG. 1A, the controller 130 can apply control signals to the scanner 120 so as to cause it to scan the beam incident on the retina in accordance with predefined parameters. More specifically, in this illustrated embodiment, the controller 130 can operate the scanner in two modes. In other words, the controller can apply control signals to the scanner so as to scan the beam in accordance with one mode or the other. In one mode, the scan parameters are suitable for selective targeting of the retinal pigment epithelial cells by the incident beam whereas in the other mode the scan parameters are suitable for causing retinal thermal photocoagulation.

Some scan parameters utilized in this embodiment include, without limitation, the beam dwell time, the incident fluence (energy deposited per unit area of irradiation), a particular scan pattern, and the number of repetitions of a scan pattern. In one exemplary embodiment, selective targeting of RPE cells in human retinas can be achieved using a separated line scan pattern (see FIG. 3B) with a dwell time shorter than about 50 μs (e.g., a dwell time in a range of about 1 ns to about 50 μs) and an incident fluence less than about 10,000 mJ/cm$^2$ (e.g., a fluence in a range of about 50 mJ/cm$^2$ to about 10,000 mJ/cm$^2$). As evident in FIG. 3B, the separated line pattern is characterized by at least two elongated treatment portions (e.g., treatment portions obtained by moving the beam across the retina along a linear dimension or illuminating a series of interconnected spots in a linear pattern) that are separated from one another by an untreated retinal portion. Further, in some embodiments, about one hundred repetitions of the separated line pattern are performed at a repetition rate of about 100 Hz in the selective targeting mode.

Alternatively, selective targeting of human RPE cells can be achieved by utilizing an interlaced line scan pattern (e.g., characterized by illuminating substantially an entire retinal target area using, e.g., a plurality of elongated treatment portions that are interlaced relative to one another) with a dwell time shorter than or equal to about 15 µs at a incident radiation fluence less than about 2000 mJ/cm$^2$.

Alternatively, the controller can operate the scanner so as to cause retinal photocoagulation. In some embodiments, for photocoagulation of RPE cells in human retinas, one hundred repeated illuminations of an interlaced line pattern (see FIG. 3C) at a repetition rate of about 100 Hz with a dwell time longer than about 15 µs at an incident radiation fluence greater than about 2000 mJ/cm$^2$ can be used. Thermal coagulation can be also achieved in alternate embodiment using repeated illuminations of an interlaced line pattern at a repetition rate of about 500 Hz.

The previously described scan parameters constitute exemplary ranges. Scan parameters outside those ranges can also be used to achieve the desired therapeutic results. For example, selective targeting of human RPE cells can be achieved in a separated line scan pattern using an incident fluence below about 10,000 mJ/cm$^2$ if the beam dwell time is lower than about 50 µs. In another example, thermal coagulation of human RPE cells can be achieved using a separated line scan pattern when adequate energy is deposited in the RPE cells during a selected time period so as to cause diffusion of sufficient heat to adjacent areas for coagulation (e.g., using an incident fluence above about 10,000 mJ/cm$^2$ and a beam dwell time above about 50 µs).

In another exemplary embodiment, a scan mode for performing selective targeting utilizes a beam characterized by parameters (such as those discussed above) within a particular therapeutic window. The therapeutic window can be defined by a ratio of the so-called ophthalmoscopic $ED_{50}$ fluence to the so-called angiographic $ED_{50}$ fluence for a particular beam dwell time; it can also be defined by the equivalent ophthalmoscopic/angiographic power ratio. As used herein, the ophthalmoscopic $ED_{50}$ fluence refers to a fluence at a particular beam dwell time that would result in ophthalmoscopically visible signs of photocoagulation in the retina (retinal whitening) with a probability of about 50%. The angiographic $ED_{50}$ fluence refers to a fluence at a particular dwell time that would result in signs of retinal damage that can observed using fundus angiography with a probability of about 50% but that are not ophthalmoscopically visible (i.e., absence of retinal whitening). In other words, the angiographic $ED_{50}$ fluence delineates a condition when selective damage to RPE cells can be witnessed. Thus, some embodiments utilize a beam that has characteristics such that it operates within a therapeutic window defined by a preferred ratio of ophthalmoscopic $ED_{50}$ to angiographic $ED_{50}$. For example, a therapeutic window that is small (e.g., very close to 1) may provide little safety margin for an operator to adjust beam characteristics between selective targeting and thermal photocoagulation. Thus, in some embodiments, the scan mode for selective targeting is characterized by scanning parameters that lead to a therapeutic window that has a value larger than about 1.5 or larger than about 2. A therapeutic window of close to 1 facilitates operation of the modality that causes thermal coagulation.

With continued reference to FIG. 1A, the controller 130 can also supply control signals to the radiation source 110 and/or one or more devices (not shown) that can control one or more optical components to alter one or more characteristics of the beam entering the scanner 120. For example, the controller can adjust a laser source to increase or decrease the emitted power (e.g., in response to control signals from the controller). In another example, the cross-sectional size of the beam incident on the retina can be changed, e.g., by utilizing techniques known in the art, so as to adjust the incident fluence. For example, this can be achieved by varying axial positions of focusing optical elements relative to one another.

Figure 1B:
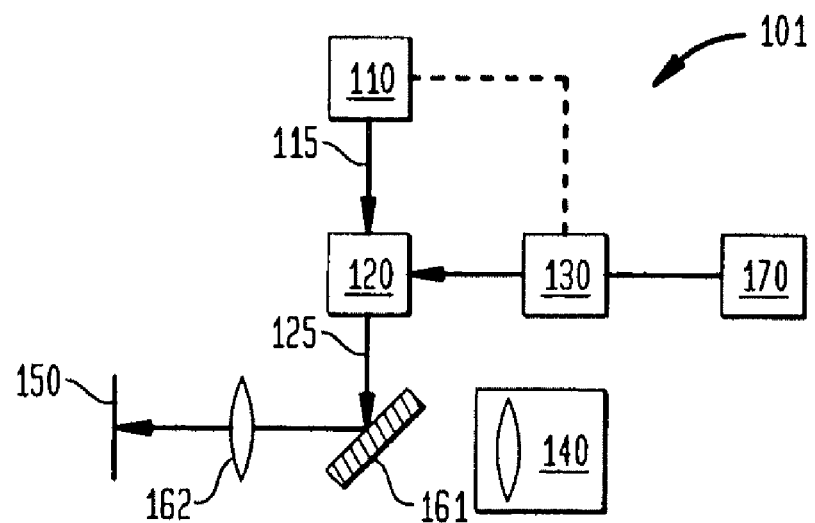
FIG. 1B depicts a schematic diagram of the optical system of FIG. 1A further including a user interface.

FIG. 1B depicts an exemplary device 101 that is similar to device 100 but also includes a user interface 170 that is in communication with the controller 130. The user interface 170 can be configured to send user selected signals to the controller 130 so as to operate a scanner 120 (and/or a source 110) with particular scan parameters, or to utilize a particular scanning mode of the scanner. For example, when the controller can operate the scanner in a selective targeting mode or a thermal photocoagulation mode, the user interface can be utilized by a user (e.g., a medical professional) to select one mode or the other. The user interface 170 can be implemented in a variety of different ways. For example, it can be embodied as a device with a knob rotatable between two positions, each position corresponding with a particular scan mode. When a particular scan mode is chosen, the user interface signals the controller to operate the scanner in accordance with the selected mode. Memory modules can be included in the controller to store predefined signals that are associated with particular scan modes, and the user interface can send commands to the controller to retrieve selected ones of those signals from memory and apply them to the scanner. In another example, the user interface can be implemented as a graphical user interface (GUI). Such a GUI can include typical screen configurations such as a drop down menus allowing a user to choose between the different scanning modes, or a touch screen with locations corresponding to activating the controller to send signals corresponding to a particular scan mode. Further, for a given scan mode (e.g., photocoagulation), such a GUI can provide options for selecting certain parameters of the scan, e.g., the scan pattern (e.g., a separated line pattern or an interlaced pattern).

Although the devices 100, 101 depicted in FIGS. 1A and 1B show a scanner 120, controller 130, and user interface 170 as physically distinct, in other embodiments, the functionality of two or all of these elements can be integrated within a single device. For example, a microcomputer can be configured to act as a user interface and a controller to receive user input and provide control signals to a scanner so as to control one or more parameters of a radiation beam. In another example, the functionality of the controller and the scanner can be integrated in a single device.

Figure 2:
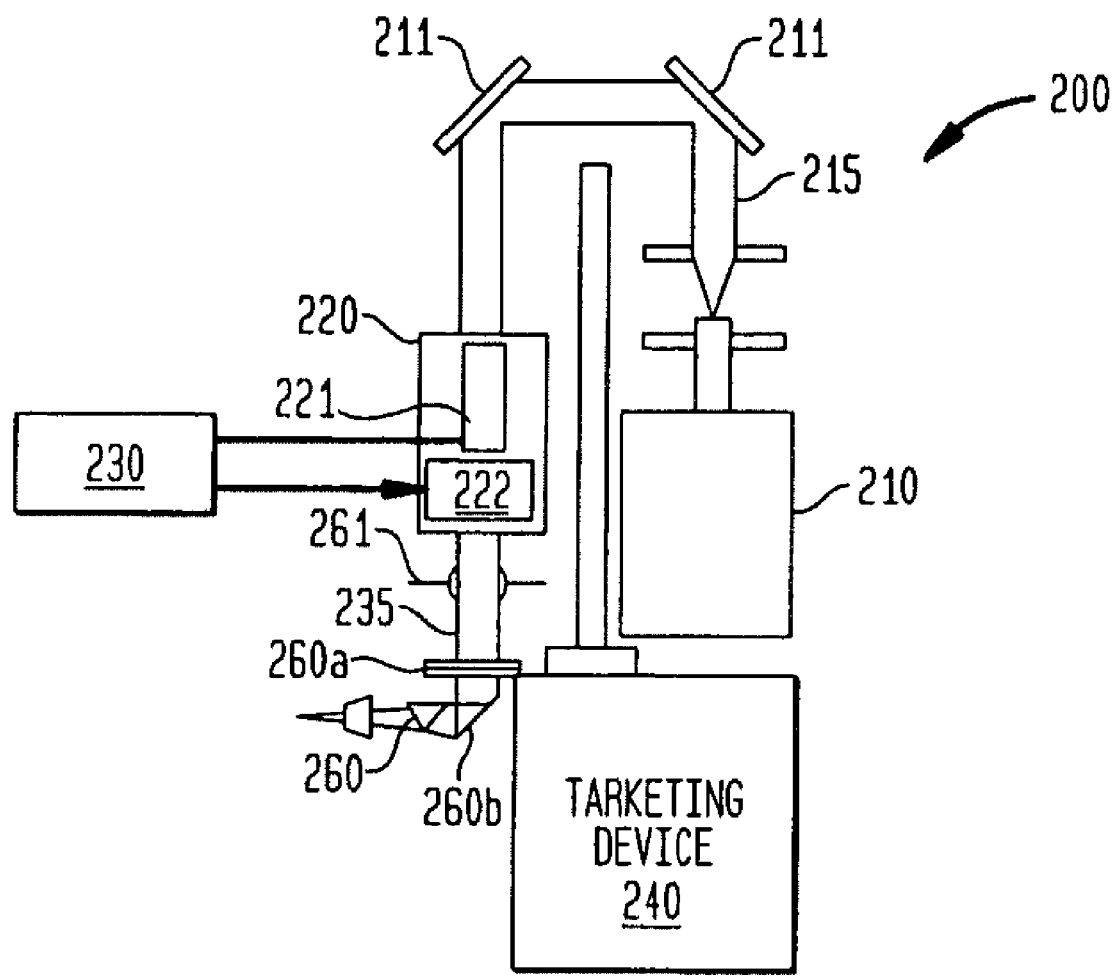
FIG. 2 depicts a schematic diagram of an exemplary implementation of an optical device shown in FIG. 1A.

The above optical devices 100, 101 can be implemented in a variety of different ways. By way of example, FIG. 2 presents an optical device 200 as one such implementation. The optical device 200 includes a laser 210 that emits a continuous wave radiation beam 215 having suitable wavelengths, such as a green wavelength (e.g., 514 nm, 532 nm or similar). Mirrors 211 direct the beam 215 to a scanner 220 that is configured to controllably move the beam in two dimensions. The scanner comprises two beam-deflecting devices 221, 222, each of which is capable of scanning the beam 215 in one of the two mutually orthogonal dimensions (both of which are orthogonal to the beam's propagation direction). A controller 230 provides control signals to the beam-deflecting devices 221, 222 to control beam movement. In this exemplary implementation, the beam-deflecting devices include two acousto-optic deflectors (AODs) that are mounted so as to provide a two-dimensional beam scan (e.g., the AODs can cause beam movement in two mutually orthogonal dimensions). The operational principles of AODs are known to those having ordinary skill in the art. Briefly, an acoustic wave propagating through an AOD crystal creates a varying index of refraction (e.g., sinusoidally) in the crystal. The varying index functions as a diffraction grating for an incident radiation beam traveling through the crystal, where the acoustic wavelength determines the grating width. Hence, the beam passing through the AOD is diffracted into various orders. In the illustrated embodiment, the first order diffraction is utilized for illuminating the retina. By sweeping the acoustic frequency, a change in the effective spacing of the optical diffraction grating occurs, thereby shifting the diffraction pattern. This, in turn, deflects the first order beam, thereby allowing the beam scan in a given direction. More particularly, in this illustrated embodiment, the first order deflected beam 235 from the beam deflecting devices 221, 222 is directed onto the retina by optical elements 260, which include a lens 260a and a mirror 260b. Further, a zero-order trap 261 captures the zero-order beam. In this implementation, the laser 210, the scanner 220, and the controller 230, are mounted on a slit lamp 240. A more thorough explanation of the controller 230 and scanner 220 is provided below.

Although in this implementation AODs are utilized as beam-deflecting devices, in other implementations, different devices can be employed. By way of example, other suitable beam deflectors include, without limitation, galvanometer scanners, rotating polygons, resonance scanners, and other types of acousto-optic or electro-optic scanners capable of moving a radiation beam in accord with functioning of the devices and methods described herein. Scanners can also utilize a combination of different beam-deflecting devices to achieve a desired movement of a radiation beam (e.g., using an AOD or resonance scanner for faster movement in one dimension and a galvanometer scanner for relatively slower movement in a second dimension).

Figure 3A:
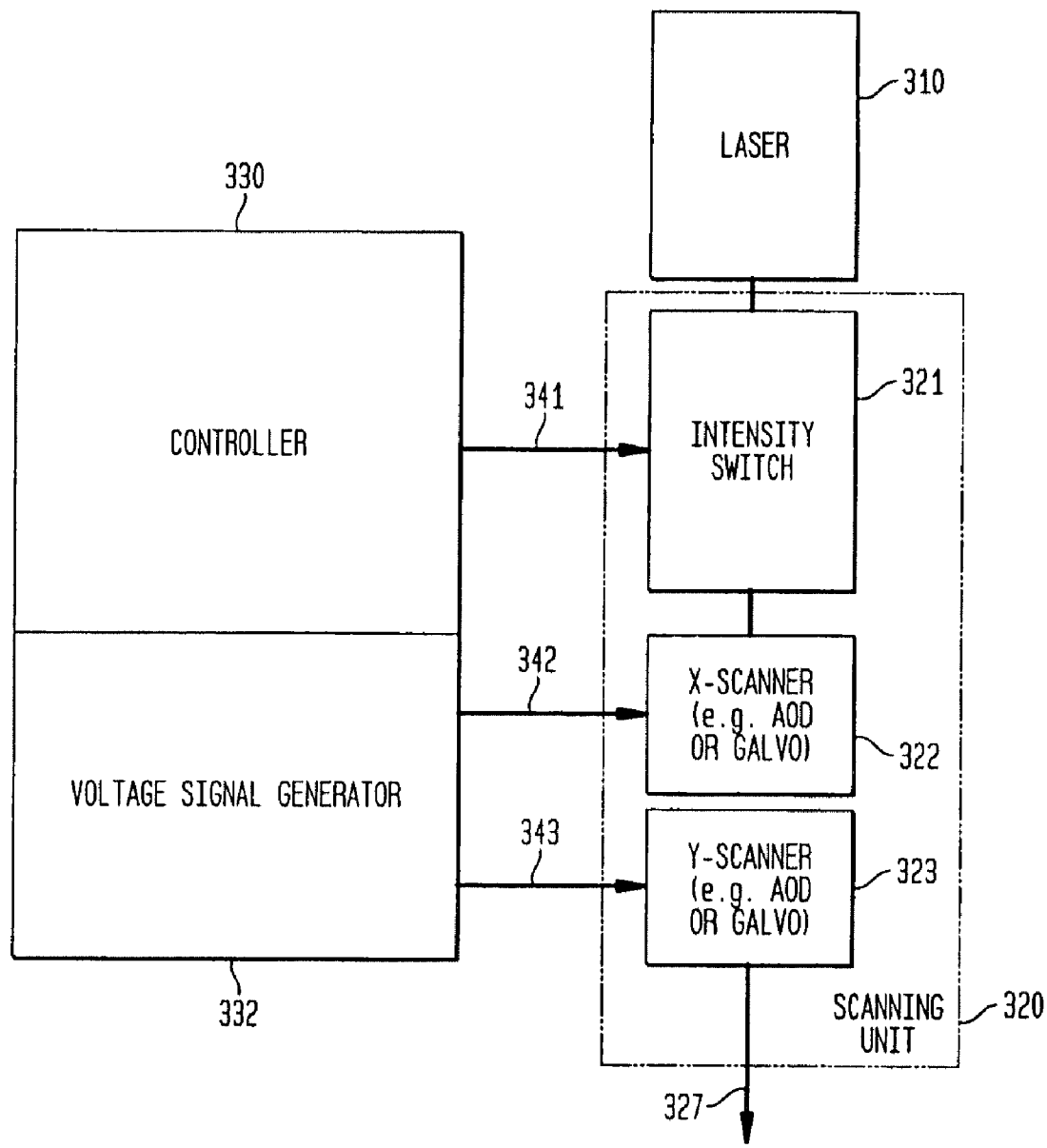
FIG. 3A is a block diagram depicting an exemplary implementation of a laser, a controller, and a scanner suitable for use in the optical device of FIG. 2.

FIG. 3A provides a block diagram depicting exemplary operational arrangement of a laser 310, a scanner 320, and a controller 330, and some of their functional components, that can be utilized in the above implementation or others. The scanner 320 can include an x-beam deflector 322 and a y-beam deflector 323 (implemented as AODs above), wherein x and y-axis are perpendicular to each other as well as a z-axis (not shown) along which the beam propagates.

Movement of the radiation beam 327 deflected by each beam deflector 322, 323 can be controlled by the controller 330 that applies scanning voltage signals 342, 343, generated by a voltage signal generator 332 having two voltage channels, to each beam deflector 322, 323, respectively. Alternatively, a separate generator may be used to produce each individual voltage signal. When AODs are utilized as beam deflectors 322, 323, each voltage signal 342, 343 can be fed to a driver of a corresponding AOD, which can include a device (e.g., a voltage-controlled oscillator (VCO)) for converting the voltage signal into a radio frequency signal for application to the AOD crystal. By changing the frequency of the radio signal (e.g., via a change in the voltage applied to the driver), a shift in the first order (or another order) of the beam passing through the AOD can be effected. In other words, the movement of the beam can be controlled by varying magnitudes of voltages applied to the AODs. When a galvanometer scanner is utilized as a beam deflector device, the angle of the beam deflection is proportional to the voltage fed to the galvanometer scanner, i.e., lower voltages position the galvanometer scanner to deflect the beam at lower angles. Clearly, the types of controllers and control signals that can be utilized are not limited to what is specifically described here, and are preferably chosen to match the characteristics of the beam deflector devices utilized in the scanner.

The scanner 320 can also include an intensity switch 321 to switch the radiation beam on and off, e.g., during selected portions of a two-dimensional scan. The AODs themselves can act as switches, as well as other devices. For example, by turning the applied radio frequency on and off, the first order beam can be selectively switched on and off. The controller 330 can apply an activation signal 341 to the switch 321 for controlling thereof. A coordinated interplay between the switch and one or more of the scanning voltages can cause the beam to move in a predefined pattern and temporal sequence, as discussed in more detail below.

Figure 3B:
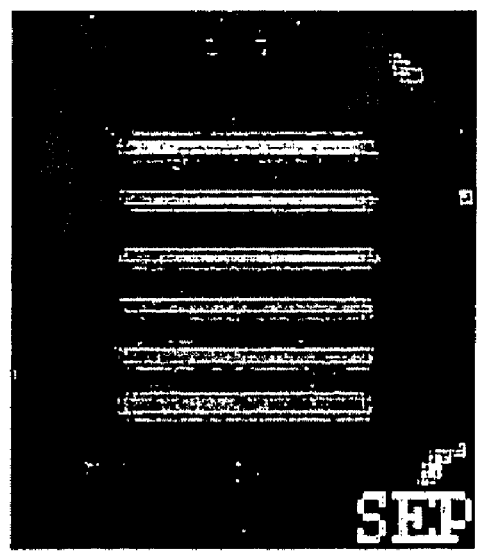
FIG. 3B is an image of a separated line pattern formed in a portion of a rabbit retina by illumination thereof in accordance with an embodiment of the invention.
Figure 3C:
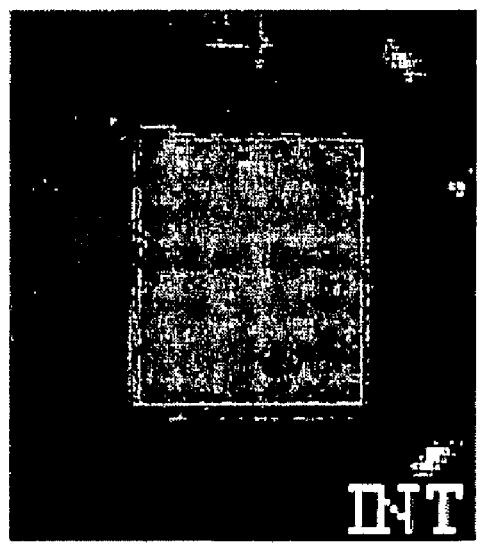
FIG. 3C is an image of an interlaced line pattern formed in a portion of rabbit retina by illumination thereof in accordance with an embodiment of the invention.

In this illustrated embodiment, the controller 330 and the scanner 320, shown in FIG. 3A, can be employed to implement at least the following two types of scan patterns: a separated line pattern (such as that depicted in FIG. 3B) and an interlaced line pattern (such as that shown FIG. 3C). The separated line pattern shown in FIG. 3B is created by controlling the two-dimensional movement of a radiation beam spot so as to illuminate a pattern comprising six equally spaced horizontal lines. In this example, the spacing between the scanned lines is about two scan line widths, though other spacings can also be utilized. The interlaced line pattern shown in FIG. 3C is created by repeating the separated line pattern shown in FIG. 3B three times, where the center of each line is displaced from that of an adjacent one by the width of a scan line (i.e., the beam's diameter) such that the entire target area is effectively illuminated.

Figure 3D:
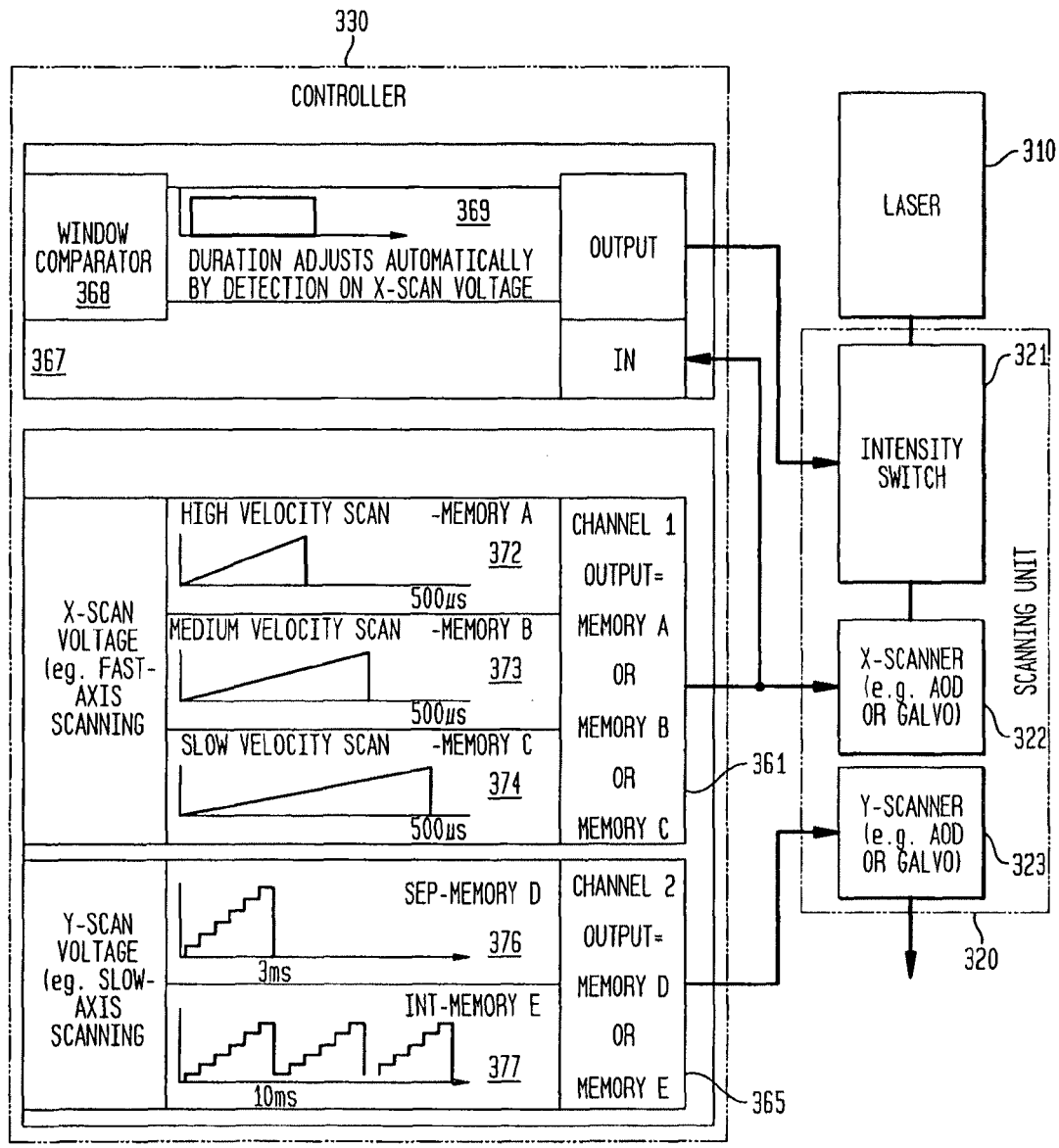
FIG. 3D is a block diagram depicting in more detail the exemplary implementation of a laser, a controller, and a scanner shown in FIG. 3A.

FIG. 3D schematically depicts that the controller 330 can be configured to store selected voltage waveforms for application to the two beam-deflecting devices. More specifically, the controller 330 includes two signal channels 361, 365, each with its associated memory, for applying control signals to beam deflectors 322, 323, respectively. The memory module (or modules) associated with each signal channel 361, 365 can store control signals (e.g., predefined waveforms, such as voltage waveforms) for application to the beam deflectors. In this implementation, the signal channel 361 is coupled to a memory module that holds three exemplary control waveforms 372, 373, 374 suitable for application to the x-beam deflector 322, while the other signal channel 365 is coupled to a memory module that stores two exemplary control waveforms 376, 377 suitable for application to the y-beam deflector 323.

With continued reference to FIG. 3D, a beam activation signal generator 367 of the controller 330 includes a window comparator 368 that utilizes the output of the signal channel 361, which is coupled to the x-beam deflector, to produce a square wave pattern 369 for application to the switch 321. In this exemplary embodiment, when the voltage signal from the signal channel 361 is between predefined upper and lower thresholds, the switch 321 allows the radiation beam generated by the laser 310 to propagate to the beam deflectors. However, when the voltage signal from the signal channel 361 is below a predefined low threshold or above a predefined high threshold, the activation signal generator turns off the switch 321 to prevent propagation of the beam to the beam deflectors. As discussed further below, the square wave signal 369 determines the endpoints of each scanned line segment by effectively preventing illumination of the target during periods 371, 375 of the ramp waveform 372, as shown in FIG. 3E and described below.

Figure 3E:
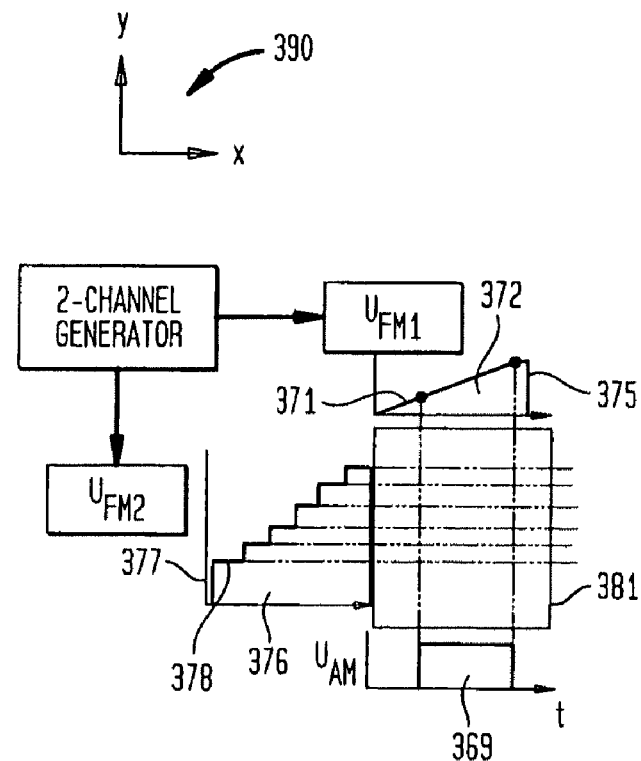
FIG. 3E depicts a schematic diagram showing the use of exemplary waveforms stored in a two channel signal generator to create a separated line pattern in accord with the implementation shown in FIG. 3D.
Figure 3F:
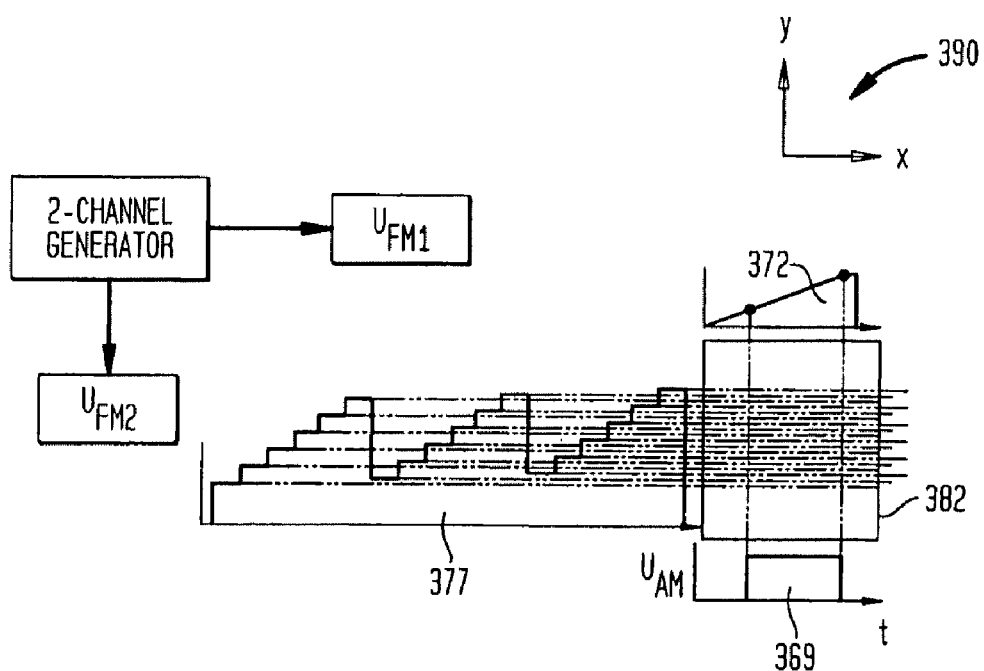
FIG. 3F depicts a schematic diagram showing the use of exemplary waveforms in a two channel signal generator to create an interlaced line pattern in accordance with the implementation shown in FIG. 3D, FIG. 4A schematically depicts a scan pattern created by illuminating a plurality of discrete retinal locations in accordance with an embodiment of the invention, FIG. 4B schematically depicts a scan pattern created by illuminating a plurality of retinal line segments in accordance with an embodiment of the invention.

Referring to FIGS. 3E and 3F, any control waveform associated with one channel can be concurrently utilized with any waveform associated with the other channel to move the beam in a two-dimensional scan pattern dictated by the combination of those waveforms. For example, as shown in FIG. 3E, a separated line pattern 381 can be formed by applying a control waveform 372 to the x-axis beam deflector 322 while concurrently applying a waveform 376 to the y-axis beam deflector 323. The ramp waveform 372 corresponds to a linear increase in voltage with respect to time. Application of this linearly-varying voltage signal to a driver of an AOD, configured to move a beam in a horizontal direction (also referred to as the x-axis as indicated by axes 390 in FIGS. 3E and 3F), results in beam movement along a horizontal line at a substantially constant velocity corresponding to the rate of change of the voltage signal. The staircase waveform 376 corresponds to a staircase pattern of voltage increases with respect to time, i.e. six successively increasing plateaus of voltage 378 that are separated by step changes in the voltage 377. Applying this staircase voltage signal to the driver of an AOD, configured to move the beam in the vertical direction (also referred to herein as the y-axis as indicated by axes 390), leads to discrete jumps (six jumps in this case) in the vertical position of the beam, where each vertical position is sustained for a time period corresponding to the temporal extension of an associated voltage plateau. Hence, by concurrent application of the waveforms 372 and 376 to the x and y deflectors, the beam can scan the retina in accordance with the separated line pattern 381. For example, as shown in FIG. 3E, if the time for one voltage plateau (e.g., the time for plateau 378) in waveform 376 corresponds with the time for the voltage to increase over the entire length of ramp waveform 372, then repeating the ramp waveform 372 six consecutive times allows formation of six line scans that are displaced in accordance with the step changes in the voltage of the staircase waveform 376.

FIG. 3F depicts that the application of a ramp waveform 372 to the x-beam deflector (the beam-deflector associated with the horizontal movement of the beam) and a staircase waveform 377 to the y-beam deflector results in a two-dimensional scan pattern on the retina characterized by an interlaced line pattern 382. In this example, the staircase waveform 377 includes three separate staircase varying voltage signals. The application of each separate staircase varying voltage signal to the beam-deflector associated with the beam's vertical movement, along with the application of a corresponding ramp waveform 372 to the beam-deflector associated with the beam's horizontal movement, result in a separated line pattern similar to that shown schematically in FIG. 3E. Each successive staircase varying voltage signal is shifted relative to a previous one such that the resultant separated line pattern is displaced vertically by approximately one line width relative to the previously formed separated line pattern. In this manner, three staggered separated line patterns are formed that in combination illuminate the entire area. Like the separated line pattern 381 formed in FIG. 3E, a square waveform 369 is created from a window comparator to provide an on/off switching signal for switching on the beam during the scan time associated with the line segments of the interlaced pattern.

As described above, an optical system of the invention can be configured to generate a plurality of scan patterns, such as a separated line pattern or an interlaced line pattern discussed above. It should be understood that other scan parameters can be utilized to alter the orientation of the line segments in the above separated line pattern as well as in the interlaced line pattern. For example, the lines can be oriented vertically, rather than horizontally. As well, lines can be formed top to bottom or bottom to top or any other order suitable for performing selective targeting or photocoagulation.

Figure 4A:
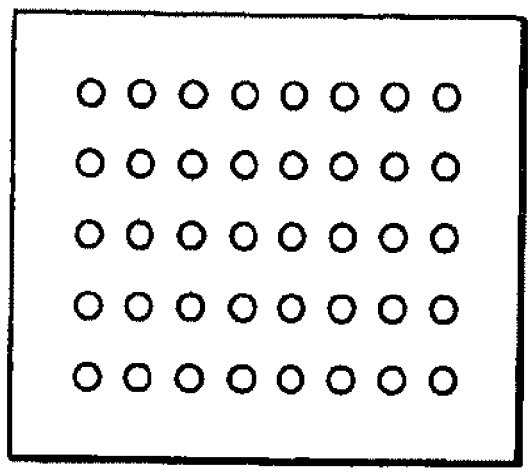
Figure 4B:
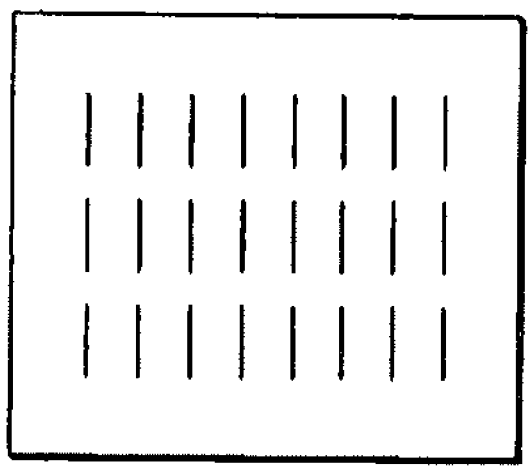

In some embodiments, the optical system can be configured to produce a fractional illumination pattern over an area of the retina requiring treatment such that each retinal treatment portion is surrounded by an untreated portion of the retina. In such a fractional pattern, a fraction of the RPE cells within a target (treatment) area are illuminated while leaving the remaining RPE cells in that target area unilluminated or at least undamaged. Such fractionally illuminated patterns can be used to achieve selective targeting of the RPE cells or photocoagulation by judicious selection of the characteristics of the illuminating beam, such as fluence and/or dwell time. A scanner can generate a fractionally-illuminated pattern using individual beam spots (FIG. 4A) or individual line segments (FIG. 4B). The separated line pattern discussed above can also be characterized as a fractionally illuminated pattern. In some embodiments, such patterns can be created, e.g., by a chopper wheel together with beam deflectors. In some cases, different portions of an entire line can be illuminated simultaneously using appropriate optics. The use of fractionally illuminated/treatment pattern can be advantageous as the non-illuminated (undamaged) retinal portions can facilitate healing of the retina after treatment.

In some embodiments, a scan pattern can be repeated multiple times to increase the total exposure of the target locations to the illuminating radiation. The number of repetitions needed to achieve either selective targeting or photocoagulation depends upon beam characteristics such as fluence, dwell time, and the repetition rate (e.g., less than about 500 Hz). In many embodiments, a number of repetitions in a range of about 1 to about 10,000, or alternatively in a range of about 1 to about 1000, or alternatively in a range of about 1 to about 100, can be utilized at a repetition rate in a range of, e.g., about 1 Hz to about 10,000 Hz, or alternatively in a range of about 1 Hz to about 5000 Hz, or alternatively in a range of about 1 Hz to about 500 Hz (e.g., about 10 Hz to about 500 Hz). It should, however, be understood that other repetition rates and numbers can also be employed. When multiple scans are utilized, a trigger generator in the controller of the optical device can generate trigger signals for initiating, and/or repeating, the scan patterns. Such trigger signals can initiate actions necessary (e.g., scanning the beam) for generating a scan pattern.

In some embodiments, the beam used to illuminate a retinal target area has a cross sectional dimension (e.g., a diameter) upon impinging the target in a range of about 5 µm to about 50 µm. In some cases, the beam cross-sectional dimension is of the order of an RPE cell diameter. This is particularly useful in a scan mode that achieves selective targeting of the RPE cells. While in many embodiments, the beam exhibits a substantially circular cross-section, in some embodiments, the beam can have a non-circular cross-section (e.g., a elliptical or other geometrical shapes). In any case, at least one dimension of the beam's cross-section is selected to have a size suitable for a particular application, e.g., the range provided above.

It should be understood that the above embodiments are exemplary, and that an optical device of the invention can be implemented in different ways. For example, a window comparator in conjunction with a function generator is not the only way to provide waveforms that control the scanning process. For example, the controller can be fully implemented in a computer. The clock of a microprocessor can be used to synchronize the controlling waveforms with respect to each other. If using a computer to generate waveforms, an activation generator can be omitted. Instead, all scan parameters can be chosen by means of a GUI (such as those described above) including the number of repetitions. By way of example, the scan process can be initiated by the user by means of a footswitch, mouse click, et cetera.

EXAMPLES

The following examples are provided to further illustrate features of the invention. They are provided only for illustrative purposes and are not intended to necessarily indicate optimal treatment results that can be obtained by practicing various aspects of the invention, nor are they intended to limit the scope of the invention.

Example 1

In Vitro Illumination of Bovine RPE Sheets

The following in-vitro experiments were performed on RPE sheets from young bovine eyes.

Optical Device

Figure 5:
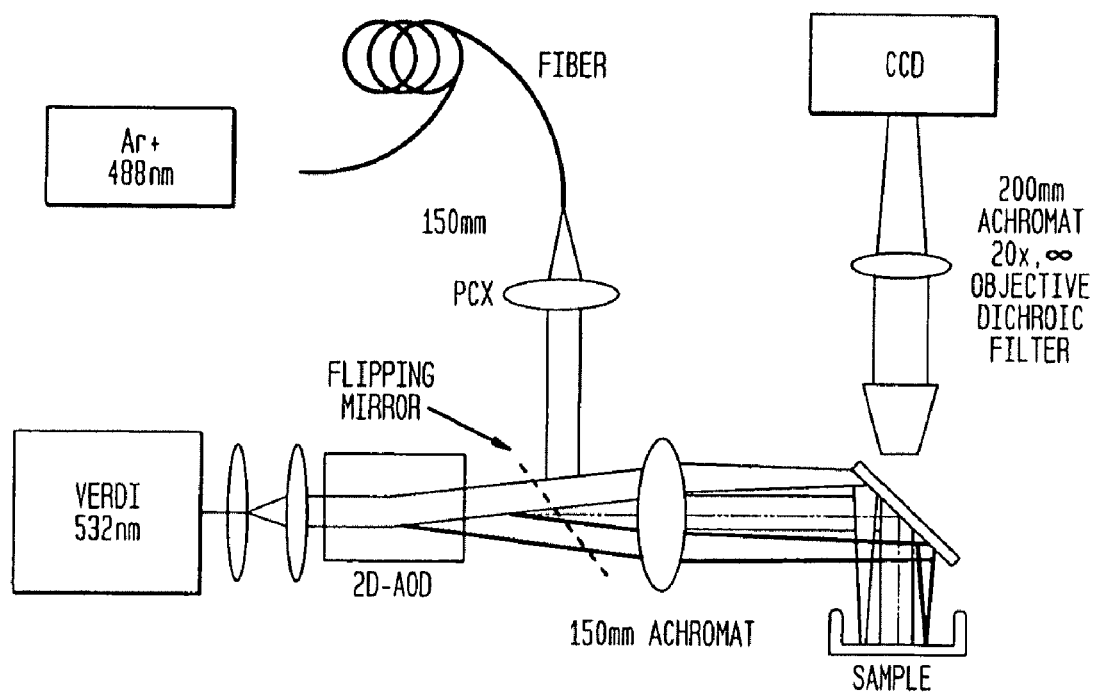
FIG. 5 depicts a schematic diagram of an exemplary optical system according to one embodiment of the invention utilized to illuminate bovine retinal pigment epithelium sheets in vitro.

A schematic diagram of the bench top optical device for the in vitro experiments is shown in FIG. 5. A 5W cw laser (VERDI, Coherent, Santa Clara, Calif., USA) served as a laser source for the illumination. An Argon Ion Laser (IN-NOVA 90, Coherent) at 488 nm, delivered through a multi-mode fiber, was used for excitation of the fluorescent cell viability probe as described below. A custom-built compound fluorescence microscope was set up to capture fluorescence images before and after illumination.

A two-dimensional (2D) acousto-optic deflector (AOD) was used to generate the scan pattern by mounting two AOD crystals (2DS-100-35-0.532, Brimrose, Baltimore, Md., USA) perpendicular to each other to allow two dimensional beam movement. To control the 2D-AOD, four electric signals are needed: one frequency modulation (FM) signal per crystal or scan axis, respectively, an amplitude modulation (AM) (switching) signal to enable the first order beam and a trigger pulse to synchronize the control unit. A suitable two-channel function generator (e.g., Tektronix, AFG320) creates the two custom-programmed FM signals. Utilizing the four fixed memories for arbitrary waveforms of the generator, the user is able to switch back and forth between different characteristics of the scan pattern. The activation signal is generated by a home built window comparator that switches the beam ON when the $FM_1$ voltage crosses the lower voltage set point that determines the left edge of the scan field. Likewise, the comparator switches the beam OFF, when $FM_1$ crosses the higher $FM_1$ reference voltage that corresponds to the right edge of the scan field. This enables the user to switch between different characteristics of the scan pattern without changing its size. For instance, it is sufficient to change the slew rate of the FM ramp signal in order to produce a different scan speed. To define the repetition rate of the scan pattern and the number of repetitions applied to each irradiation site, an additional digital pulse generator (Tektronix, PFG5105) is used to trigger the entire control unit.

The optical device was aligned so that the central acoustic frequency of the full bandwidth of the 2D-AOD defines the optical axis of the device. The scan angles for the line and the frame scans were produced as half angles around this optical axis to minimize coma, which may occur due to any scanning process, as the beam by default is steered off the optical axis. To focus the first order beam a single achromatic lens was placed one focal distance from the midpoint between the two crystals of the 2D-AOD, forming a nearly telecentric optic, in order to minimize curvature of the scanners' focal plane.

The spot diameter and beam profile were determined on a stationary spot centered in the scan pattern using the knife-edge method. The scan speed was measured by scanning the laser spot along a microscope scale (100 Div./1 mm), detecting the transmitted light with a photodiode and measuring the time between two minima produced when the spot would run over a cross hair of the scale. Using this methodology, the spot diameter on the sample was measured to be 20 μm. The scan field was nearly square with a length of the scan lines and a height of the pattern of 300 μm.

Preparation and Illumination of In-Vitro Samples

RPE sheets from young bovine eyes were used for in vitro experiments. Samples of roughly 15 mm diameter were prepared from the posterior segment of each eye. After removal of the neuroretina, a viability assay was prepared from each sample by incubation in CalceinAM. CalceinAM is a non-fluorescent dye. Because it is also non-polar, it diffuses into cells where it is reduced by esterase to Calcein, which performs as the actual fluorescence marker. The spectrum of Calcein shows an excitation peak at a wavelength of 490 nm and an emission maximum at 520 nm. Calcein is polar and thus, is unable to leave the cells. Live cells therefore will appear bright under fluorescence illumination conditions whereas dead cells, whose membrane integrity has been compromised, will appear dark.

After incubation each sample was placed in a Petri dish. A lid with a hole in the center held the sample in place. The dish was filled with phosphate buffer solution and the opening in the lid closed with a microscope cover glass. After irradiation, a fluorescence image was captured and the damage evaluated according to the viability assay.

Samples were exposed to various levels of laser power using the separated lines scan pattern (SEP) to produce a scan pattern of area 300 μm×300 μm with six scan lines spaced by 60 μm between line centers. The power of the illumination beam was varied to determine the Effective Dose 50% ($ED_{50}$) for RPE cell damage. $ED_{50}$ corresponds to a probability of 50% that an exposed cell will be killed.

Three different parameters were varied: dwell time, number of repetitive exposures, and repetition frequency. Dwell times of 3 μs and 10 μs is were utilized. As well, ten and one hundred repetitive exposures were applied with repetition frequencies of 100 Hz and 500 Hz for each exposure time. All measurements were performed in duplicates.

Results

Figures 6A, 6B, 6C:
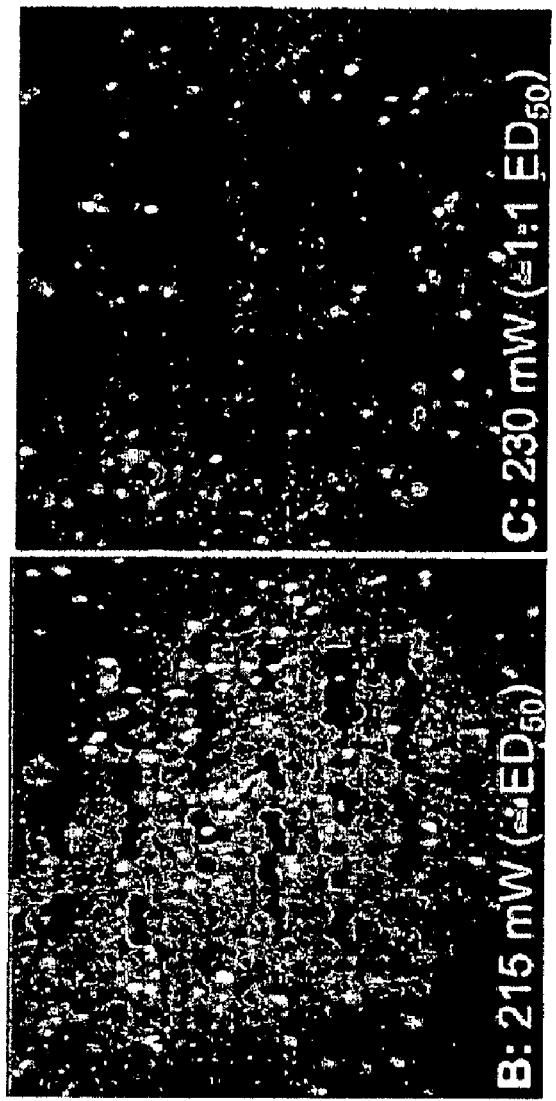
FIG. 6A is an image of a bovine retinal pigment epithelium sheet in vitro after illumination with the separated line pattern of FIG. 3B using the system of FIG. 5 with a beam power of 170 mW.
FIG. 6B is an image of a bovine retinal pigment epithelium sheet in vitro after illumination with the separated line pattern of FIG. 3B using the system of FIG. 5 with a beam power of 215 mW.
FIG. 6C is an image of a bovine retinal pigment epithelium sheet in vitro after illumination with the separated line pattern of FIG. 3B using the system of FIG. 5 with a beam power of 230 mW.

Calcein viability assays performed after irradiation of bovine RPE sheets showed separate lines of dark cells in the fluorescence images resembling the applied scan pattern, as presented in FIGS. 6A-6C. All scans used a beam to irradiate locations for a dwell time of 3 μs at 100 Hz utilizing 10 repetitions of the pattern. The beam utilized in FIG. 6A corresponds to about 0.8 of the average power required to achieve $ED_{50}$. The image shows that few exposed cells were damaged. The beam used in FIG. 6B had a power of 215 mW, corresponding to about the average required to achieve $ED_{50}$. As can be seen, lines of dead cells appear to be confined to a width of about one or two cells wide. Cells in between the scan lines remained viable, suggesting selectivity within the RPE monolayer. A 230 mW beam is used to create the image in FIG. 6C, corresponding to about 1.1 of the average power to achieve $ED_{50}$. In this image, all exposed cells were damaged and widening of the lines was observed.

Results for scans performed in vitro under varying scan parameters are presented in Table 1 in terms of the average power needed to achieve $ED_{50}$, $ED_{15}$, and $ED_{85}$. The fluence of the beam used to irradiate RPE cells to achieve $ED_{50}$ is also listed. For the Gaussian beam utilized here, the fluence along the center of the scan line is given by:

$$\text{Fluence} = \sqrt{\frac{2}{\pi}} \frac{2 P\tau}{d_0^2}$$

where P is the power of the beam, $\tau$ is the dwell time, and $d_0$ is two times the $1/e^2$ radius of the Gaussian profile.

TABLE 1

Results from in vitro scanning of bovine RPE cells

| Repetition Frequency | Parameters | $ED_{50}$ [mW] | $ED_{15}$ [mW] | $ED_{85}$ [mW] | $ED_{50}$ fluence [mJ/cm$^2$] |
|---|---|---|---|---|---|
| 100 Hz | 3 µs, N = 10 | 221 | 212 | 230 | 264 |
| | 3 µs, N = 100 | 206 | 201 | 210 | 247 |
| | 10 µs, N = 10 | 130 | 126 | 135 | 519 |
| 500 Hz | 3 µs, N = 10 | 222 | 216 | 228 | 265 |
| | 3 µs, N = 100 | 182 | 180 | 184 | 218 |
| | 10 µs, N = 10 | 130 | 126 | 135 | 519 |

The $ED_{50}$ power for cell damage decreased by increasing the number of repetitions/repetitive scans (N) from 10 to 100 repetitive exposures. Increasing the dwell time from 3 µs to 10 µs (i.e., slowing down the velocity of the flying spot) also decreased the necessary power to damage the cells. A dependence of the $ED_{50}$ on the repetition frequency was not observed. However, reversible shrinking of the tissue occurred during irradiation with 500 Hz repetition frequency, when the sample was exposed to power levels three times above the damage threshold ($ED_{50}$) while scanning 100 repetitive 10 µs exposures.

Example 2

In Vivo Illumination of Rabbit Eyes

The following in-vivo experiments were performed in rabbit eyes.
Optical Device

Figure 7:
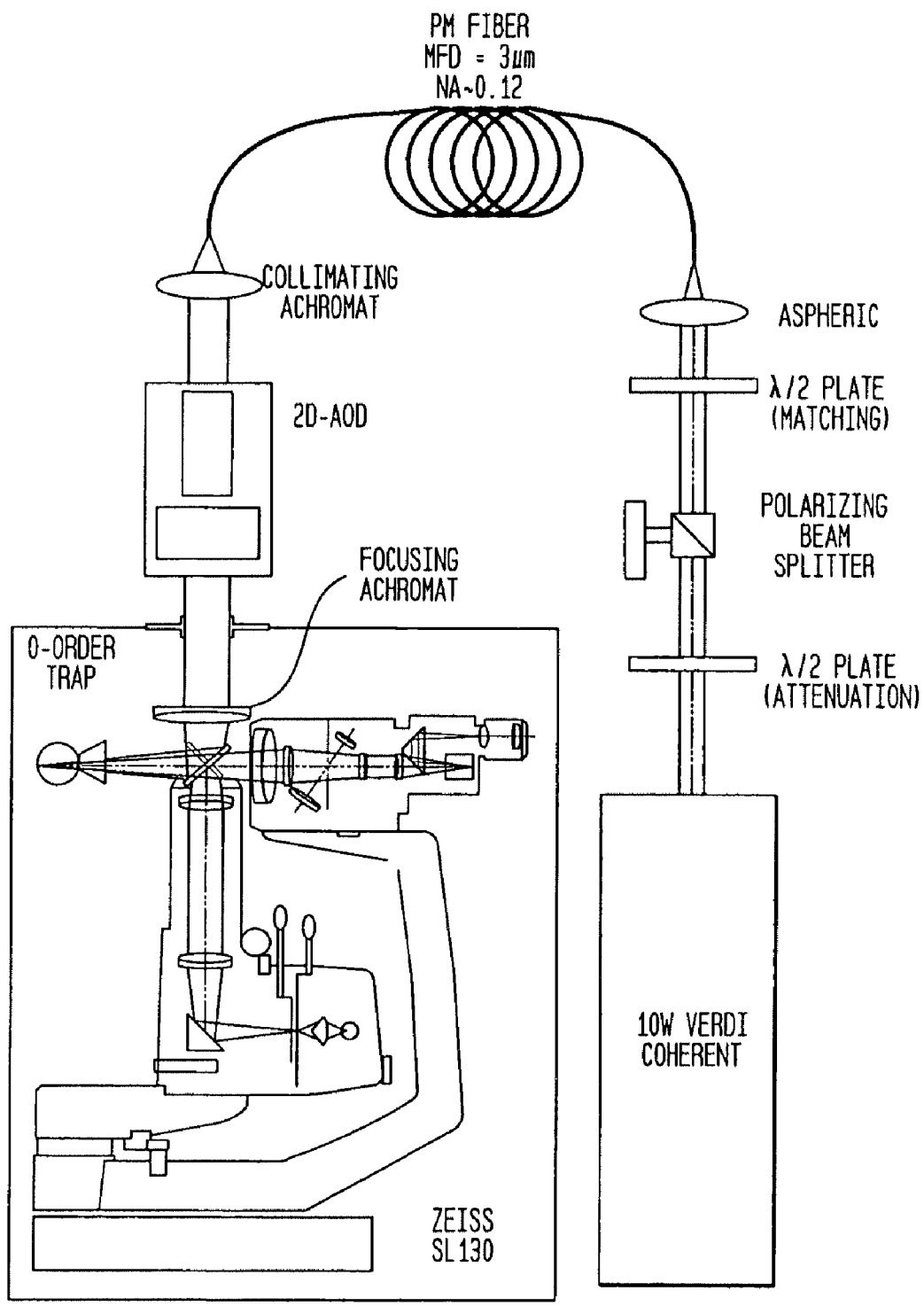
FIG. 7 depicts a schematic diagram of an exemplary optical system according to one embodiment of the invention utilized to illuminate rabbit retinas in vivo.

For the in vivo experiments, an optical system was developed to fit on top of a slit lamp as shown in the schematic diagram of FIG. 7. Such a system is considerably smaller than the bench top system utilized with the in vitro experiments. The emission (532 nm) of a cw-laser (VERDI V-10, Coherent) was coupled into a polarization maintaining single mode fiber (PM fiber) (HB450, Fibercore Ltd., UK). PM fiber was employed to preserve diffraction limited beam characteristics and because linear polarization was required for optimal operation of the AOD. Its use limited the power that could be delivered to the setup to about 300 mW. With a typical diffraction efficiency of two AODs (64%) the highest possible power entering the eye was 185 mW.

A scanner design as utilized in the in vitro experiments was mounted with its mechanical components, collimating and focusing optics vertically on top of the slit lamp (SL130, Zeiss, Oberkochen, Germany). The PM fiber output and the collimator were mounted on a six-axis stage (x, y, z, tip, tilt, rotate) to match the Bragg condition and the preferred polarization direction of the 2D-AOD. As shown in FIG. 7, a mirror, placed between the two lenses of the stereo objective of the slit lamp, directed the first order beam horizontally away from the objective into the eye, running along the optical axis of the slit lamp.

In order to achieve the same size of the scan pattern on the retina as used in the in vitro experiments, the scan field in air was enlarged to a width and height of 450 µm, with 90 µm spacing between line centers for the SEP pattern. The energy to the rabbit eye was applied through a Goldman contact lens, which together with the optics of the rabbit eye magnified all distances on the retina by a factor of 0.66, making the scan area 300 µm×300 µm, with 60 µm spacing, on the retina.

The $1/e^2$ spot diameter was measured, by means of the knife-edge method, to be 27.5 µm in air. The spot size on the rabbit retina was calculated to be 18 µm after taking into account the Goldman contact lens and the optics of the rabbit eye. Differentiation of knife-edge measurement suggested that the beam was nearly Gaussian. Translation of the knife-edge in small increments through the beam waist along the optical axis led also to determination of the beam propagation around the focus. In the device utilized, the irradiance applied to the target site varied by only 10% over a range of +/−200 µm on either side of the focus.
Preparation and Illumination of Rabbit Eyes Dutch belted rabbits were chosen because density and location of light-absorbing pigments in the fundus of rabbits are rather uniform and similar to that of the human eye. The animals were anesthetized and placed in a holder system that allowed tilting and rotating of the animal relative to the slit lamp. The contact lens was placed onto the mydriatic eye using methylcellulose 2% as contact gel. The lens was attached to the animal holder by a special clamping system to prevent unfavorable movements.

Ophthalmoscopically visible marker lesions for orientation were placed in each eye. The selective treatment lesions that are ophthalmoscopically invisible were placed between these marker lesions using different power levels in a pre-defined grid pattern. A total number of 308 lesions in 12 eyes covered a variety of parameter sets. For each parameter, $ED_{50}$ was determined in two eyes of different individuals.

One hour after irradiation, fluorescence angiography was performed by injection of 10% sodium fluorescein into the ear vein. If the RPE is damaged, the blood-ocular-barrier is compromised and fluorescein can pool from the choriocapillaris into the subretinal space. Under fluorescence illumination, lesions will then appear bright whereas undamaged areas will remain dark. Thus, fluorescein angiography was used to detect damages of the RPE barrier and identify lesions. $ED_{50}$ values were calculated using probit-analysis. Endpoint was based on the appearance of angiographically visible lesions. Thus, the angiographic $ED_{50}$ is defined as the set of conditions resulting in a 50% probability of the appearance of fluorescence using the above described technique. In contrast, the ophthalmoscopic $ED_{50}$ is defined as the set of conditions resulting in a 50% probability of the appearance of ophthalmoscopically visible grayish lesions from the coagulation of photoreceptors as a result of beam exposure.

The repetition frequency for all parameter sets in vivo was 100 Hz. Both separated line scan patterns (SEP) and interlaced line scan patterns (INT) were performed. For the SEP scan pattern, consisting of six separated lines, the speed was varied to create 7.5 µs and 15 µs exposures in the center of the scan line. Ten and one hundred repetitions per irradiation site were applied for both scan speeds. For the INT pattern, 21 interlacing lines without spacing, ten repetitions of 7.5 µs exposure and one hundred repetitions of 15 µs exposure were tested as presumably the least or most invasive parameters, respectively. In the INT pattern, adjacent lines are created with a time delay of about 3 milliseconds. During this time, cells adjacent to the first line of pattern will have been heated by heat diffusion from the exposed, neighboring cells so that the returning spot adds additional energy to the adjacent cells.
Results RPE cells can be damaged selectively in vivo as indicated by leakage of the fluorescein dye in the form of the scan pattern with concurrent lack of visible coagulation of the neurosensory retina as depicted in FIGS. 8A-8C. Ophthalmoscopically invisible lesions can be visualized by fundus angiography, where fluorescein can pool into the eye in those areas where the blood-ocular barrier has been compromised by laser mediated RPE cell damage. FIG. 8C presents a schematic diagram of the various types of irradiation performed in the fundus of a rabbit eye. Two columns of marker lesions, marked as "M," served as orientation points. The marker lesions were produced using the INT scan pattern at a slow scan speed. Selective lesions created with a high scanning speed (marked as regions 1, 2, 3, and 4) were positioned between the marker lesions. Blocks 1 and 2 were produced using a SEP scan pattern, and blocks 3 and 4 were produced using an INT scan pattern. FIG. 8A is a fundus photograph of the scanned region minutes after irradiation. The grayish, visible lesions on the left of the image are the marker lesions (coagulation). All four selective lesions to the right of the marker lesions are ophthalmoscopically not visible in FIG. 8A (i.e. no retinal whitening). FIG. 8B shows the fluorescence image of the same site of FIG. 8A one hour post irradiation. Here, the marker lesions appear dark in the center with a bright rim, and previously non-visible selective lesions show up as hyper fluorescent.

Results for scans performed in vivo under varying scan parameters are presented in Table 2 in terms of the average power needed to achieve angiographic $ED_{50}$, $ED_{15}$, $ED_{85}$, and the fluence of the beam used to achieve $ED_{50}$ as calculated using the same equation as presented earlier. Angiographic ED was determined by angiographic visibility of lesions.

TABLE 2

Results from scanning of rabbit RPE cells in vivo

| | Parameters | $ED_{50}$ [mW] | $ED_{15}$ [mW] | $ED_{85}$ [mW] | $ED_{50}$ fluence [mJ/cm$^2$] |
|---|---|---|---|---|---|
| Parameters yielding SELECTIVE targeting | 7.5 µs, N = 10, SEP | 92 | 89 | 95 | 340 |
| | 7.5 µs, N = 100, INT | 67 | 62 | 72 | 248 |
| | 7.5 µs, N = 10, INT | 69 | 64 | 74 | 255 |
| | 15 µs, N = 10, SEP | 66 | 63 | 69 | 482 |
| | 15 µs, N = 100, SEP | 57 | 56 | 59 | 416 |
| | 15 µs, N = 100, INT | 45 | 41 | 48 | 329 |
| COAGULATION | 15 µs, N = 100, INT | 75 | -/- | -/- | 511 |

For the SEP pattern, the cell damage $ED_{50}$ decreased with exposure time from 93 mW with 7.5 µs to 66 mW with 15 µs exposure. This corresponds to an increase of the angiographic $ED_{50}$ radiant exposure from 340 mJ/cm$^2$ to 482 mJ/cm$^2$. Angiographic $ED_{50}$ (both in terms of power and radiant exposure) also decreased with increasing number of exposures N. With the available maximum power of the system, the ophthalmoscopic damage threshold was not reached, as indicated by visible retinal coagulation (i.e., the appearance of visible grayish white lesions), for all irradiation parameters except for 100 repetitions of 15 µs exposures with an interlaced scan pattern. Thus, in terms of a "Therapeutic Window" (TW), which is the ratio of ophthalmoscopic $ED_{50}$ over angiographic $ED_{50}$, for SEP patterns tested here, the TW is greater than 3.2 since the maximum available power of 185 mW was 3.2 times higher than the angiographic $ED_{50}$.

Irradiating with the INT scan pattern, which uses interlacing lines without spacing between lines, reduced the threshold power required for cell damage compared to separated lines. Ophthalmoscopic threshold was reached for the most "invasive" parameter used—100 repetitions with 15 µs exposure time (see row labeled "coagulation" in table 2). For this case the TW was 1.7, i.e., the neural retina was coagulated with a fluence corresponding to 1.7 times the angiographic $ED_{50}$.

Example 3

In Vivo Illumination of Rabbit Retina using a SEP Scan Pattern to Achieve Selective Targeting and Thermal Coagulation Rabbit retina was illuminated in vivo using a SEP scan pattern to achieve selective targeting in one instance, and thermal photocoagulation in another instance. Histological sections of the irradiated areas were prepared after irradiation to assess the laser-induced damage.

Figure 9:
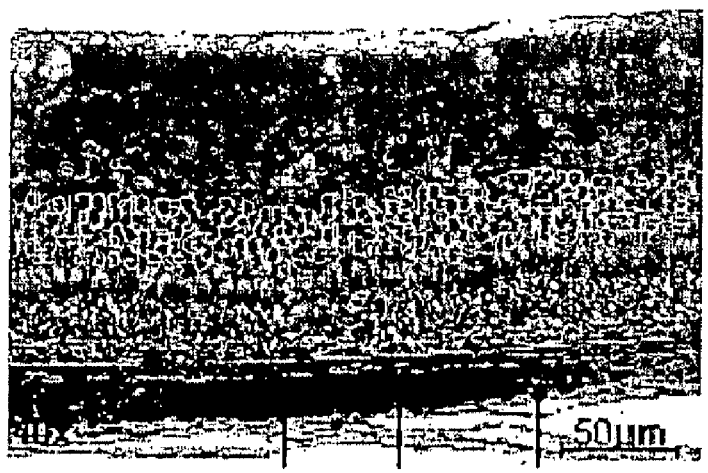
FIG. 9 is an image of a histological section of a selective lesion produced by irradiating rabbit retina in vivo.
Figure 10:
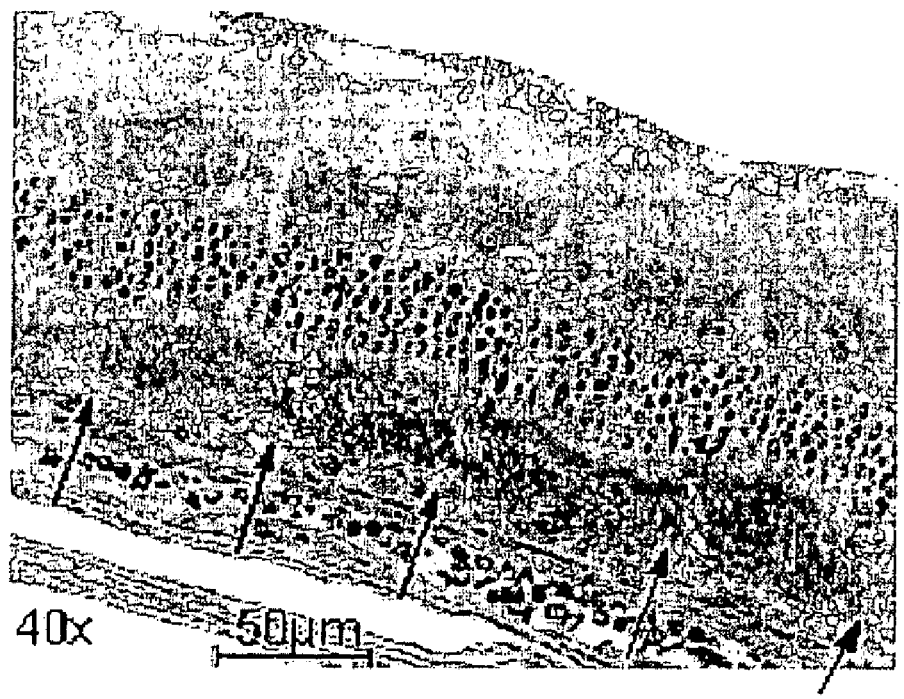
FIG. 10 is an image of a histological section of a coagulated lesion in a rabbit retina in vivo produced by the same optical system utilized to produce the lesion shown in FIG. 9.

FIG. 9 presents a histological section of selectively damaged rabbit RPE cells using a SEP scan pattern. The beam had a dwell time of 7.5 µs and a fluence of 470 mJ/cm$^2$, the latter corresponding to about 1.5 times the $ED_{50}$ fluence. Ten repetitions of the SEP scan pattern were performed. The arrows point to individually damaged RPE cells. The photoreceptors are intact. In contrast, FIG. 10 presents a histological section showing coagulated photoreceptors using a beam dwell time of 30 µs. Ten repetitions were performed using an incident fluence of 1800 mJ/cm$^2$ (about 3 times the $ED_{50}$ fluence). The arrows point to coagulated photoreceptors.

Those having ordinary skill in the art will appreciate that various modifications can be made to the above embodiments without departing from the scope of the invention. For example, the controller and the scanner in optical devices of the invention can be implemented differently than those discussed herein so long as they provide the requisite functionality for practicing the invention.

What is claimed is:

1. An apparatus for applying radiation to a subject's retina, comprising:
   a radiation source for generating a radiation beam having one or more wavelengths suitable for absorption by retinal pigment epithelial cells,
   at least one optical component for directing the beam onto the retina,
   a scanner optically coupled to the source for controllably moving the beam in two dimensions to scan the beam over the retina, and
   a controller in communication with the scanner to apply control signals thereto for adjusting movement of the beam to illuminate a plurality of retinal locations according to a scan pattern,
   wherein the controller is capable of operating the scanner in any of at least two scan modes, one of the scan modes being suitable for selective targeting of retinal pigment epithelial (RPE) cells and another scan mode being suitable for causing thermal photocoagulation in the retina,
   wherein the controller operates the scanner in the selective targeting mode by scanning with a beam characterized by parameters within a therapeutic window defined by a ratio of an ophthalmoscopic $ED_{50}$ fluence to an angiographic $ED_{50}$ fluence for a selected beam dwell time, wherein the ophthalmoscopic $ED_{50}$ fluence is a fluence at the selected beam dwell time that results in ophthalmoscopically visible indicators of photocoagulation of the retina, and the angiographic $ED_{50}$ fluence is a fluence at the selected dwell time that results in indicators of selective damage to RPE cells that are visible using angiography, but are not ophthalmoscopically visible;
   wherein the controller operates the scanner in the selective targeting mode when the ratio has a value greater than about 1.5;
   wherein the controller operates the scanner to produce a fractional illumination pattern over the retina in which a fraction of retinal pigment epithelial cells within the retina are illuminated, the fractional illumination pattern comprising a plurality of treatment portions of the retina that are exposed to the radiation beam, and wherein each treatment portion is surrounded by an untreated portion of the retina that is not exposed to the radiation beam; and wherein the fractional illumination pattern comprises a plurality of beam spots on the retina, each beam spot corresponding to one of the treatment portions.

2. The apparatus of claim 1, wherein the beam imparts a fluence greater than about 50 mJ/cm$^2$ to the retina.

3. The apparatus of claim 1, wherein the scan mode suitable for selective targeting is characterized by a beam imparting a fluence less than about 10,000 mJ/cm$^2$ to the retina and having a dwell time less than about 50 microseconds.

4. The apparatus of claim 1, further comprising a user interface in communication with the controller for selecting the scan modes.

5. The apparatus of claim 1, wherein the controller applies control signals to the scanner for causing selective targeting of the retinal pigment epithelial cells in the illuminated locations.

6. The apparatus of claim 1, wherein the scanner comprises two beam-deflecting devices, each capable of scanning the beam in one of the two dimensions.

7. The apparatus of claim 6, wherein at least one of the beam-deflecting devices comprises an acousto-optic deflector.

8. The apparatus of claim 7, wherein the controller applies predefined control signals to the acousto-optic deflector so as to cause a movement of the beam along one of the dimensions.

9. The apparatus of claim 8, wherein the controller comprises a memory module for storing a plurality of predefined control waveforms suitable for application to the acousto-optic deflector.

10. The apparatus of claim 1, wherein the beam has a cross-sectional dimension that is about the size of a retinal pigment epithelial cell.

* * * * *